United States Patent [19]
Adahan

[11] Patent Number: 5,484,270
[45] Date of Patent: Jan. 16, 1996

[54] PUMP PARTICULARLY USEFUL IN RESPIRATOR APPARATUS AND EXHALATION VALVE ASSEMBLY THEREFOR

[76] Inventor: Carmeli Adahan, Netivei Am 11, Ramot Gimmel, 97552 Jerusalem, Israel

[21] Appl. No.: 202,950

[22] Filed: Feb. 28, 1994

[51] Int. Cl.⁶ .......................... F04B 35/04; A61M 16/00
[52] U.S. Cl. .......................... 417/415; 417/534; 417/551; 128/205.13; 128/205.16
[58] Field of Search .................. 128/204.28, 205.13, 128/205.16, 205.18; 417/415, 534, 551, 569

[56] References Cited

U.S. PATENT DOCUMENTS

| | | | |
|---|---|---|---|
| 1,713,219 | 5/1929 | Eisenhauer | 417/415 |
| 3,918,447 | 11/1975 | Inkster et al. | 128/205.16 |
| 3,932,066 | 1/1976 | Eyrick et al. | 128/205.16 |
| 4,145,165 | 3/1979 | Perkins et al. | 417/418 |
| 4,276,003 | 6/1981 | Perkins et al. | 417/415 |
| 4,493,614 | 1/1985 | Chu et al. | 417/22 |
| 4,807,616 | 2/1989 | Adahan | 128/204.21 |
| 4,823,787 | 4/1989 | Adahan | 128/203.27 |
| 4,836,198 | 6/1989 | Gates | 128/205.18 |
| 4,941,469 | 7/1990 | Adahan | 128/205.18 |

FOREIGN PATENT DOCUMENTS 2155624   5/1973   Germany ................. 417/415

Primary Examiner—Richard A. Bertsch
Assistant Examiner—William Wicker
Attorney, Agent, or Firm—Ladas & Parry

[57] ABSTRACT

A reciprocating pump particularly useful in ventilator apparatus includes a piston reciprocatable axially within a cylinder and dividing its interior into an inlet chamber and an outlet chamber, a wall fixed within the inlet chamber, and a drive housing fixed to the wall. The drive housing includes a motor, a rotor rotatable by the motor, a nut rotatable within the drive housing, and a screw threadedly coupled at one end to the nut and fixed at its opposite end to the piston. The piston is substantially unrestrained for axial and rotary movement such that forward and reverse rotation of the nut by the motor reciprocates the screw and the piston axially of the cylinder, and also permits the screw and the piston to rotate with respect to the cylinder to thereby even out wear between the piston and cylinder.

10 Claims, 6 Drawing Sheets

PUMP PARTICULARLY USEFUL IN RESPIRATOR APPARATUS AND EXHALATION VALVE ASSEMBLY THEREFOR

FIELD AND BACKGROUND OF THE INVENTION

The present invention relates to pumps, and particularly to pumps useful in respirator apparatus. The invention also relates to an exhalation valve assembly useful in such pumps and respirator apparatus. Respirator apparatus, sometimes called ventilator apparatus, is widely used for administering artificial respiration or ventilatory assistance to a patient. Examples of such apparatus are described in my prior U.S. Pat. Nos. 4,807,616, 4,823,787 and 4,941,469.

An object of the present invention is to provide a novel pump particularly useful in respirator apparatus and providing a number of important advantages as will be described more particularly below. Another object of the invention is to provide an exhalation valve assembly also particularly useful in the novel respirator apparatus.

BRIEF SUMMARY OF THE INVENTION

According to one aspect of the present invention, there is provided a reciprocating pump particularly useful in ventilator apparatus, comprising: a pump housing having an inlet at one end, an outlet at another end, and a cylinder between the inlet and outlet; a piston reciprocatable axially within the cylinder and dividing its interior into an inlet chamber communicating with the inlet, and an outlet chamber communicating with the outlet; a fixed wall within the inlet chamber and having a passageway therethrough communicating with the inlet; a drive housing fixed to the wall and including a motor having a rotor rotatable by the energization of the motor; a nut rotatable within the drive housing and fixed to the rotor to rotate therewith; and a screw threadedly coupled at one end to the nut and fixed at its opposite end to the piston. The piston is supported by a rotatable bearing between the nut and the drive housing, and a seal between the piston and the cylinder.

According to further features in the described preferred embodiments, the piston is substantially unrestrained for axial and rotary movement such that forward and reverse rotation of the nut by the motor reciprocates the screw and the piston fixed thereto axially of the cylinder, and also permits the screw and the piston fixed thereto to rotate with respect to the cylinder, to thereby even out wear between the piston and cylinder.

According to still further features in the preferred embodiments of the invention described below, the pump further includes a noise isolator interposed between the rotatable bearing and the drive housing. A tubular sleeve is fixed to the drive housing in alignment with the screw for receiving and enclosing one end of the screw opposite to that fixed to the piston. The tubular sleeve includes a lubricating wick for lubricating the screw when received therein.

The foregoing features permit the pump to be constructed with very low mechanism inertia, allowing reversal of the piston travel direction very quickly (approximately 5 milliseconds). Thus, a respirator including such a pump may be operated to provide a very rapid rate of breaths, such as 150 breaths per minute, as required for respiration of newborn babies, as well as slower rates required in other applications.

According to another aspect of the invention, there is provided respirator apparatus comprising: a pump housing having an inlet at one end, an outlet at the other end, and a cylinder between the inlet and outlet; a piston reciprocatable axially within the cylinder and dividing its interior into an inlet chamber communicating with the inlet, and an outlet chamber communicating with the outlet; an exhalation valve coupled to the pump housing outlet via a coupling fitting; and a one-way valve in the coupling fitting leading to the atmosphere. The one-way valve is normally closed, but automatically opens by a negative pressure within the coupling fitting to connect the interior of the coupling fitting to the atmosphere.

Such a one-way valve thus allows the patient to draw ambient air in case the respirator fails and there is an internal blockage or restriction. In conventional respirators, a one-way valve, commonly called an H-valve, is generally mounted on the patient air delivery tubes externally of the respirator. By providing this valve as an integral part of the coupling fitting which couples the pump housing to the exhalation valve, a more compact and portable arrangement is produced.

According to a still further aspect of the invention, there is provided an exhalation valve assembly particularly useful in the novel respirator apparatus, comprising: a housing having an inlet port connectible to an outlet of a pump, an outlet port for connection to the patient, an exhalation port leading to the atmosphere, a valve member connecting the outlet port either to the inlet port or to the exhalation port, and a control chamber for controlling the operation of the valve member in response to the pressure in the control chamber. The exhalation valve assembly further includes a control valve for controlling the pressure in the control chamber to increase the pressure therein during inspiration to cause the valve member of the exhalation valve to connect the outlet port to the inlet port, and to decrease the pressure in the control chamber during exhalation to thereby cause the valve member of the exhalation valve to connect the outlet port to the exhalation port of the exhalation valve. The control valve further includes presettable means for presetting a predetermined partial pressure in the control chamber during exhalation to thereby preset the exhalation pressure to open the exhalation valve.

For example, it is frequently desired to maintain a fixed low pressure in the patient line during exhalation so that the patient's lungs remain slightly inflated. On the other hand, the pressure on the line during exhalation must not be excessive as this can impede exhalation. The foregoing feature of the invention conveniently enables the pressure during exhalation to be preset to the desired value according to the particular situation.

In the described preferred embodiment, the presettable means includes a solenoid having an armature which controls the pressure in the control chamber of the exhalation valve according to the energization of the solenoid. Thus, by presetting the current to be supplied to the solenoid, one can conveniently control the pressure delivered to the patient during both inspiration and exhalation.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
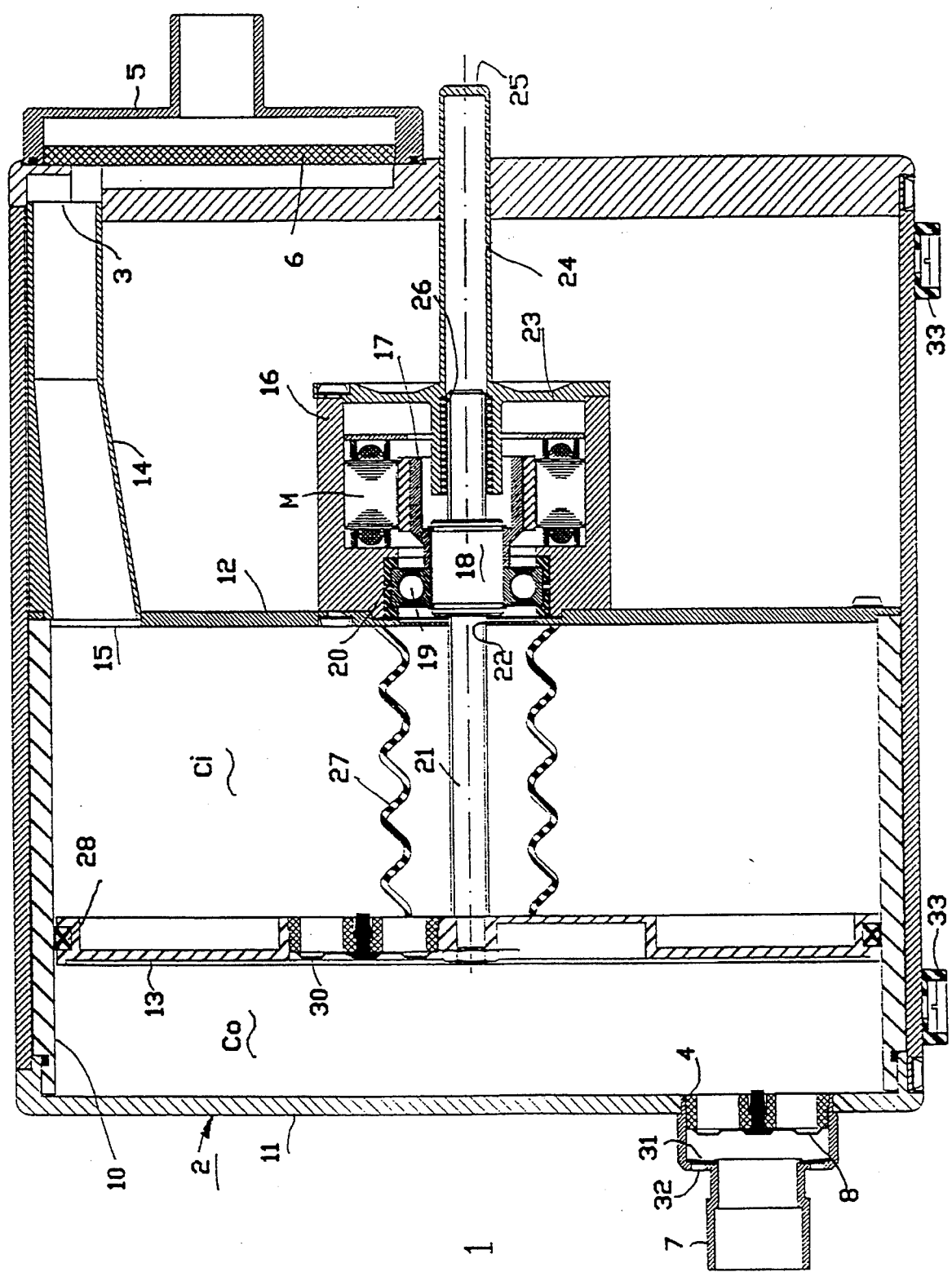
FIG. 1 is a vertical sectional view illustrating one form of single-acting pump constructed in accordance with the present invention and particularly useful in respirator apparatus.
Figure 1A:
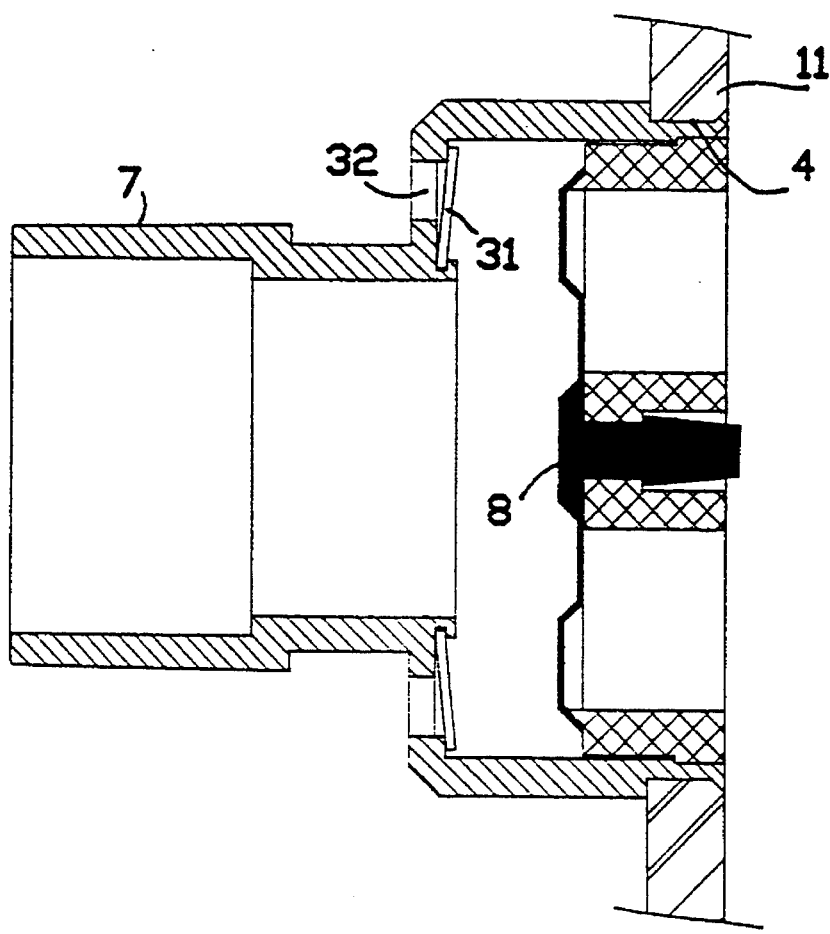
FIG. 1a is an enlarged fragmentary view of FIG. 1.

The Pump of FIGS. 1 and 1a

The pump illustrated in FIG. I is particularly useful in respirator apparatus for administering artificial respiration or ventilation. The pump includes a housing 2 formed with an inlet port 3 at one end, and an outlet port 4 at the opposite end. The inlet port 3 receives an inlet fitting 5 provided with a filter 6 for removing solid particles from the air inletted into the pump housing. The outlet port 4 receives a coupling fitting 7 for coupling the outlet to the exhalation valve via a delivery tube, as will be described below, and is provided with a one-way valve 8 to permit air to flow only outwardly of the pump housing.

The interior of housing 2 includes a cylinder 10 which is closed at one end by end wall 11 of the housing, and at the opposite end by a partition wall 12 fixed within the housing. A piston 13 is reciprocatably mounted within cylinder 10 to divide the interior of the cylinder into an inlet chamber $C_i$ and an outlet chamber $C_o$. The inlet chamber $C_i$ communicates with the inlet 3 via an intake tube 14 and an opening 15 formed in the fixed partition wall 12; whereas the outlet chamber $C_o$ communicates with the outlet via the one-way valve 8 and the coupling fitting 7.

Piston 13 is reciprocatable axially within cylinder 10 by means of a motor M disposed within a drive housing 16 mounted to the fixed partition wall 12. Motor M includes a rotor 17 fixed to a nut 18 which is rotatably mounted by a rotary bearing 19 to the drive housing 16 via a rubber noise isolator 20.

Nut 18 threadedly receives a threaded screw 21 passing through an opening 22 in the fixed partition wall 12. One end of threaded screw 21 is fixed to piston 13, and the opposite end is threadedly received within nut 18. The end of the drive housing 16 facing the inlet 3 of the pump housing is closed by an end wall 23 integrally formed with a tubular sleeve 24 which receives the end of the threaded screw 21.

Tubular sleeve 24 is of a length to receive the complete length of the threaded screw 21 in its extreme rightmost position and is closed by an end wall 25 so as to completely enclose the screw 21 and thereby to protect it from outside contamination. The inner diameter of sleeve 24 is enlarged at its inner end and receives a felt lubricating wick 26 for continuously lubricating the screw 21 as it is reciprocated within the tubular sleeve 24.

A bellows 27 encloses screw 21. Bellows 27 is secured at one end to piston 13 and at the opposite end to the fixed partition wall 12, to thereby protect the part of the screw between the piston and the partition wall against contamination. Bellows 27 also produces a seal for chamber $C_1$ preventing air inside it from escaping outwards through the motor housing which is unsealed.

Piston 13, including its threaded screw 21, is supported for movement within cylinder 10 by the previously-mentioned rotary bearing 19 within drive housing 16, and by a rotary seal 28 along the outer circumference of the piston. Bellows 27 and seal 28 permit both axial and some rotary movement of piston 13, so that the piston is substantially unrestrained for both such movements. Thus, rotation of nut 18 receiving screw 21 will move screw 21, and thereby also piston 13, axially, and will also permit the piston to rotate somewhat with respect to cylinder 10. The latter function evens out the wear between piston 13 and cylinder 10.

Piston 13 is formed with an opening receiving a one-way valve 30 permitting air to flow only in the direction from the inlet chamber Ci to the outlet chamber Co. This one-way valve, and also one-way valve 8 within the outlet 4 which permits air flow only outwardly of the outlet chamber Co, may be, for example, umbrella valves, so-called because of their umbrella shape.

A further one-way valve 31 (see FIG. 1a) is provided in the coupling fitting 7 attached to the outlet port 4 of the pump housing. One-way valve 31 may be in the form of a valve leaf normally biassed to close an opening 32 leading to the atmosphere, but deflectable (rightwardly, FIGS. 1 and 1a) if there is a negative pressure within the coupling fitting 7, to thereby connect the interior of the coupling fitting to the atmosphere. Valve 31 thus serves the same function as the H-valve usually mounted on the patient air delivery hose, to permit the patient to inhale ambient air in case the respirator fails and there is an internal blockage or restriction.

The pump housing 2 is further provided with supporting feet 33 to permit it to be supported on any suitable horizontal surface.

The operation of the pump illustrated in FIG. 1 will be apparent from the above description. Thus, when motor M is energized in one direction, its rotor 17 rotates nut 18 to move screw 21, and thereby piston 13, in one direction, e.g., leftwardly, to contract the outlet chamber Co, thereby forcing air out through the outlet one-way valve 8. During this movement of piston 13, its one-way valve 30 is closed, thereby preventing air in the inlet chamber Ci from entering the outlet chamber Co.

When motor M is energized in the opposite direction, screw 21, and thereby piston 13, are moved in the opposite direction, e.g., rightwardly. This expands the outlet chamber Co and contracts the inlet chamber Ci, whereby air from the inlet chamber is drawn into the outlet chamber via one-way valve 30. One-way valve 8 is closed and thereby does not permit any air to flow out of the outlet chamber.

Piston 13 is supported substantially unrestrained for both axial movement and rotational movement by rotary bearing 19 and seal 28. Thus, during its axial displacement by the rotation of nut 18, it will be free to undergo some rotational movement, which has been found to be advantageous in that this evens out the wear around the circumference of seal 28 to extend its life.

In case the respirator fails and there is an internal blockage or restriction in the respirator, the patient can still inhale by virtue of the one-way valve 32 in the coupling fitting 7, since the latter valve will open by a negative pressure produced within the coupling fitting during inspiration under such conditions.

It will thus be seen that in the pump of FIG. 1 each complete reciprocatory cycle of piston 13 produces one output stroke of air via the outlet port 4. The pump illustrated in FIG. 1 is therefore a single-acting pump.

Figure 2:
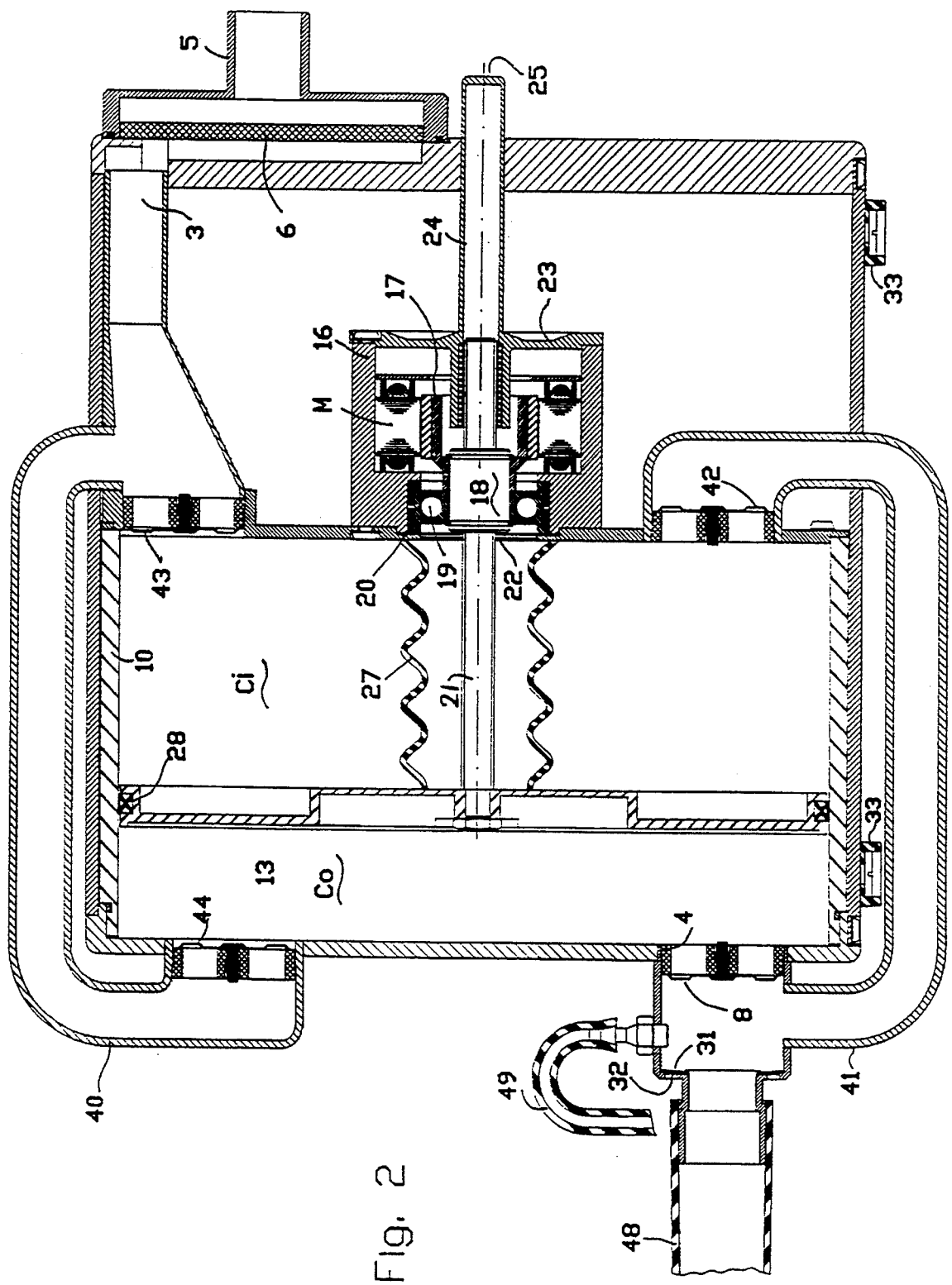
FIG. 2 is a view similar to FIG. 1 illustrating a dual-acting pump constructed in accordance with the present invention.

The Pump of FIG. 2

FIG. 2 illustrates a dual-acting pump of substantially the same construction as in FIG. 1 except modified so as to produce two output strokes for each reciprocatory cycle of the piston. To faciliate understanding, those parts in the pump of FIG. 2 which are common to those in FIG. 1 carry the same reference numerals.

The dual-acting pump illustrated in FIG. 2 includes, in addition to the parts common to the pump of FIG. 1 as described above, also an inlet conduit 40 connecting the inlet 3 to both the chamber Ci and chamber Co, and an outlet conduit 41 connecting the outlet 4 to both chamber Ci and chamber Co. The outlet 4 includes the one-way valve 8 as in the single-acting pump illustrated in FIG. 1 permitting air flow only outwardly from the outlet chamber Co to the respective end of the outlet duct 41. The latter end of duct 41 serves the same function as the outlet coupling fitting 7 in FIG. 1, and is provided with the one-way valve 31 normally closing the vent opening 32. Another one-way valve 42 is provided at the opposite end of the outlet conduit 41 communicating with the inlet chamber Ci, and permitting only outflow of air from that chamber to the outlet conduit.

Piston 13 in the dual-acting pump illustrated in FIG. 2 does not include a one-way valve. Instead, the pump of FIG. 2 includes a one-way valve 43 at one end of the inlet conduit 40, permitting air flow only into the inlet chamber Ci, and a second one-way valve 44 at the opposite end of the inlet conduit 40, permitting air flow only into the outlet chamber Co.

It will be seen that the dual-acting pump illustrated in FIG. 2 operates in the same manner as the single-acting pump illustrated in FIG. 1, except that it provides two pumping strokes for each reciprocatory cycle of the piston 13.

Figure 3:
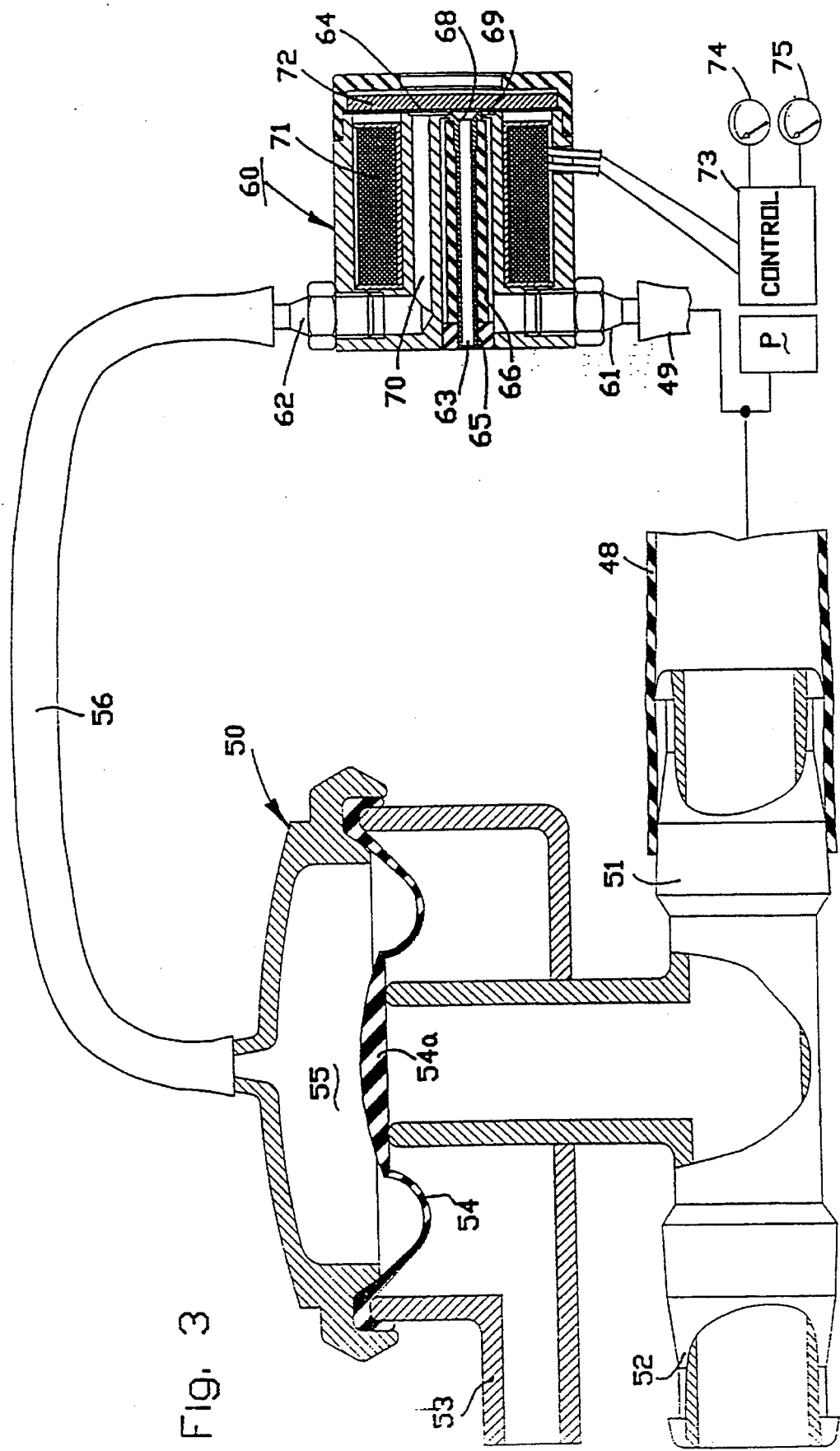
FIG. 3 is a longitudinal sectional view illustrating respirator apparatus including one form of exhalation valve assembly constructed in accordance with the present invention and its connections with the pump of FIGS. 1 or 2.
Figure 4:
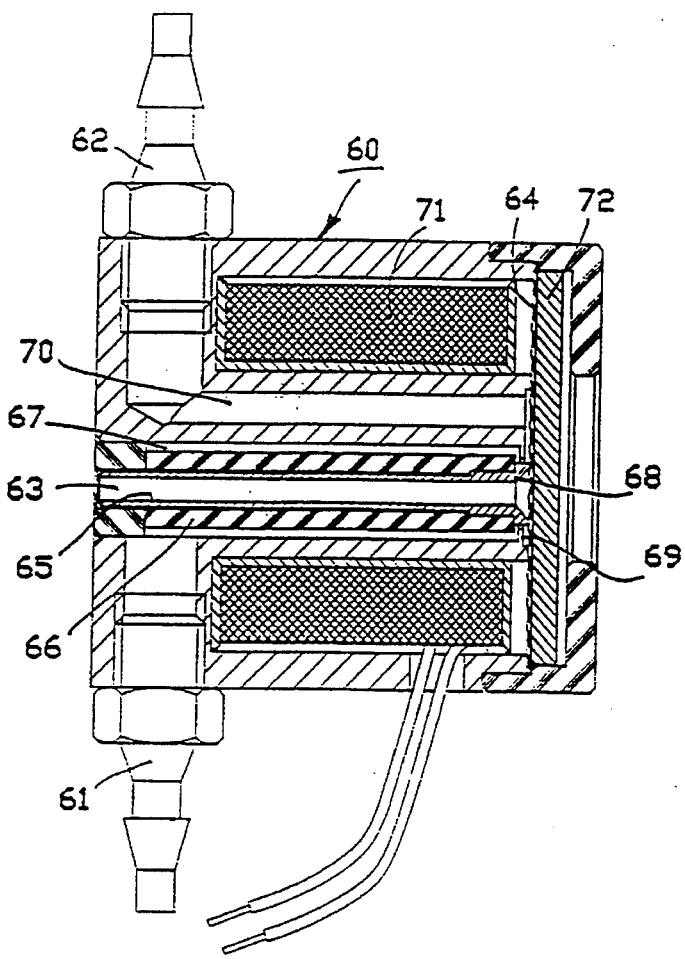
FIGS. 4 and 5 are enlarged views illustrating two different conditions of the control valve in the exhalation valve assembly of FIG. 3.
Figure 5:
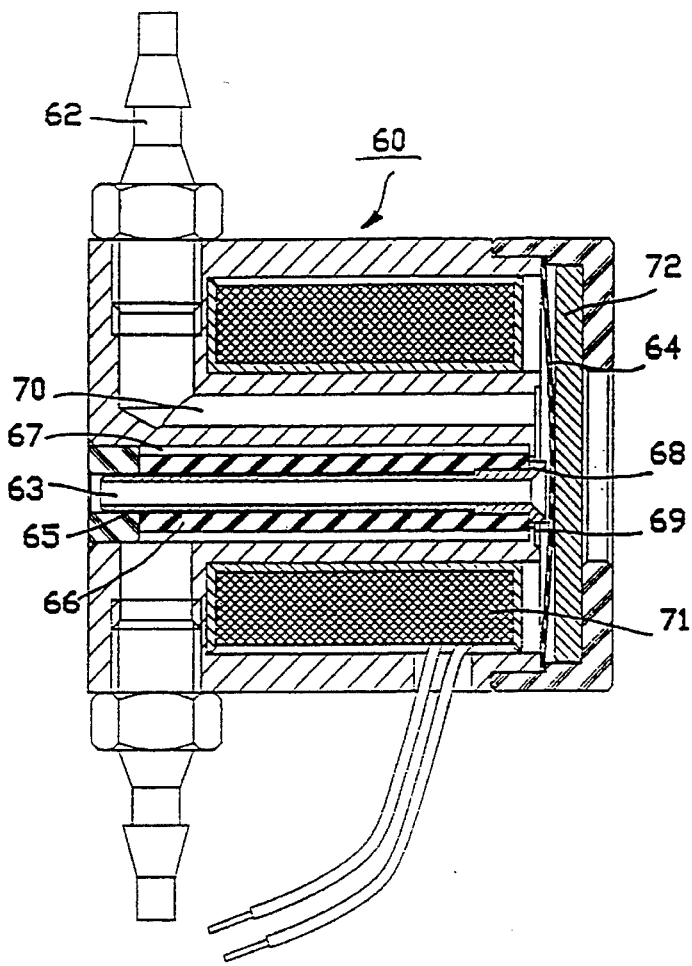

The Respirator of FIGS. 3–5

FIG. 3 illustrates respirator apparatus including a pump P and an exhalation valve assembly for delivering the air produced by the pump to the patient. The pump P may be either the single-acting pump of FIG. 1, or the dual-acting pump of FIG. 2. For purposes of example, it is described below using the dual-acting pump of FIG. 2. The outlet of that pump, as shown in FIG. 2, includes an air delivery tube 48, and a pressure control tube 49, both connected to the respective end of the outlet conduit 41 serving as the coupling fitting 7 in FIG. 1.

The exhalation valve assembly is connected to the pump P as illustrated in FIG. 3 for delivering the air outputted by the pump P to the patient. It includes an exhalation valve 50 and a control valve 60 for controlling the operation of the exhalation valve in order to permit inspiration and exhalation by the patient. As will be described more particularly below, the control valve 60 enables the pressure during both inspiration and exhalation to be preset, e.g., in order to fix the low pressure so that the patient's lungs remain slightly inflated, and/or to prevent a high pressure which may be injurious to the patient.

The exhalation valve 50 includes an inlet port 51 connected to the air delivery tube 48 at the outlet of the pump P; an outlet port 52 for connection to the patient; an exhalation port 53 leading to the atmosphere; and a valve member 54 connecting the outlet port 52 either to the inlet port 51 or to the exhalation port 53. Valve member 54 is in the form of a diaphragm seatable on a valve seat 54a and controlled by the differential pressure between that at the inlet port 51 on one side of the diaphragm, and a control chamber 55 on the opposite side of the diaphragm. Control chamber 55 is connected by a tube 56 to the control valve 60, such that the operation of the control valve controls the pressure within chamber 55, and thereby the operation of valve member 54.

Control valve 60 includes an inlet port 61 connected via tube 49 to the outlet of pump P; a control port 62 connected via tube 56 to control chamber 55 of the exhalation valve 50; a vent 63 leading to the atmosphere; and a control member 64. Control member 64 is movable to a first position (shown in FIGS. 4 and 4a) connecting the control port 62 to the inlet port 61, or to a second position (shown in FIGS. 5 and 5a) connecting the control port 62 to the vent 63.

Control port 62 is connectible to the inlet port 61 to transfer the pressure at the inlet port (which is the same as the pump P outlet pressure) to control chamber 55 of the exhalation valve 50. This moves diaphragm 54 to its closed position (illustrated in FIG. 3), and thereby permits inspiration by the patient via inlet port 51 and outlet port 52. Control port 62 of the control valve 60 is also connectible to vent 63 to vent control chamber 55 of the exhalation valve 50 to the atmosphere in order to permit the patient to exhale via outlet port 52 and exhalation port 53 leading to the atmosphere. As will be described below, control valve 60 may also be preset to control the pressure within control chamber 55 of the exhalation valve 50 during exhalation, to thereby preset the exhalation pressure by the patient to cause the patient's lungs to remain slightly inflated during exhalation (which for many patients is beneficial) without requiring an excessive pressure during exhalation such that it may be injurious to the patient.

As shown in FIGS. 4 and 5, control member 64 of the control valve 60 is a diaphragm which selectively controls two passageways: one passageway is between the inlet port 61 and the control port 62, whereas the second passageway is between the control port 62 and the atmospheric vent 63.

Control valve 60 includes a hollow metal stem 65 enclosed by an elastomeric tube 66 movable within a bore 67 extending through the control valve. One end of hollow stem 65 defines the atmospheric vent 63. The opposite end of the hollow stem is formed with an enlarged tip 68 which is engageable by diaphragm 64, such that the diaphragm biasses the hollow stem 65 and its elastomeric sleeve 66 leftwardly (FIGS. 4 and 5). Elastomeric sleeve 66, however, is pre-compressed so that it biasses the metal stem 65 rightwardly, i.e., against diaphragm 64, with the elastomeric sleeve 66 limiting against an annular flange 69 fixed within the control valve 60. The control valve includes a further passageway 70 leading from the control port 62 to diaphragm 64.

Control valve 60 further includes a solenoid comprising a coil 71 and an armature or clapper 72 which is attracted magnetically towards the housing of the control valve according to the magnetic force generated by the current passing through coil 71. Armature 72 may be positioned according to any one of three modes, depending on the relative forces applied to it:

(1) A pressure relief mode, in which the armature 72 is urged to the right by diaphragm 64 (see FIG. 5) since the diaphragm is exposed to the pressure at outlet 62. In this relief position, the pressure at outlet 62 causes the diaphragm to disengage from tip 68 of stem 65, to allow air to escape from the outlet port 62 to the atmosphere via atmospheric vent 63, thereby reducing the pressure in the control chamber 55.

(2) A "hold" mode, in which armature 72 presses diaphragm 64 against the tip 68 of stem 65 (FIG. 4). In this position, there is no flow between the outlet port 62 and atmosphere or inlet port 61, so that the pressure at the outlet port 62 is maintained.

(3) A "pressure" mode, in which armature 72 presses diaphragm 64 against tip 68 of stem 65, and further pushes the stem (leftwardly) to create a passage between inlet port 61 and outlet port 62. In this mode, pressure at the outlet port is increased until it reaches the pressure of the inlet port 61, or until such time as the pressure applied to diaphragm 64 overcomes the magnetic force applied to armature 72, moving it to the right to seal off the passageway in annular flange 69. In this mode, modulating the current through coil through coil 71 will thus modulate the pressure at port 62, and thereby modulate the pressure in the control chamber 55 of the exhalation valve 50.

It is important to note that in the "hold" mode (2) above the armature is moving back and forth in a very small travel, pivoting around its resting point on the bottom edge. This pivotal movement is substantially frictionless, and thus provides a modulating valve that produces as essentially hysteresis-free control of the exhalation valve.

It is also important to note that the diaphragm 64 acts as a force transmitting means, as well as a dual seal, one for the tip 68, and one on its periphery sealing the inside of the solenoid to atmosphere. Resilient elastomeric sleeve 66 is also a triple function member, in that: it acts as a spring to urge hollow stem 65 to the right; it acts as a seal with respect to annular flange 69; and it also acts as a seal with respect to the inlet port 61. The foregoing arrangement of sleeve 66, tip 68, flange 69 and diaphragm 64 assures that the passage to the atmosphere via vent 63 cannot be open when the inlet passage 67 is open.

The current through the solenoid coil 71 is controlled by a control circuit, shown schematically at 73. Control circuit 73 cyclically controls coil 71 to provide full or partial energization during inspiration, and no energization or partial energization during exhalation, as may be preset by manual presetting means shown schematically as knobs 74 and 75, respectively. Thus, presetting knob 74 controls the cycles of energization of coil 71 and thereby the rate of inspiration/exhalation, whereas knob 75 controls the energizing current to the coil during inspiration and exhalation and thereby the fixed pressure during inspiration and exhalation.

The operation of the respirator apparatus illustrated in FIG. 3 will now be described particularly with reference to FIGS. 4, 4a, 5 and 5a.

Figure 4A:
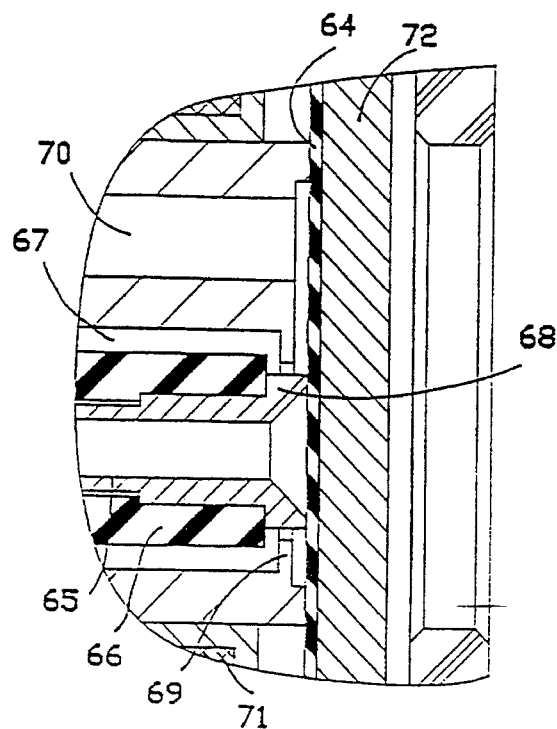
FIG. 4a and 5a are enlarged fragmentary views of the control valve of FIGS. 4 and 5, respectively.

FIGS. 4 and 4a illustrate the position of the diaphragm 64 in the control valve 60 during inspiration. At this time, full energizing current is supplied by control circuit 73 to solenoid coil 71 causing the solenoid to draw its armature 72 to the limit position illustrated in FIGS. 4 and 4a. In this limit position, armature 72 presses diaphragm 64 against the metal tip 68 of the hollow stem 65, closing the passageway from control port 62 to the atmospheric vent 63 via the hollow stem. The force applied by armature 72 against diaphragm 64 is sufficient to move the hollow stem 65, including its elastomeric sleeve 66 leftwardly, and thereby away from annular flange 69, to open the passageway from the inlet port 61 through bore 67 and passageway 70 to the control port 62. Accordingly, at this time, the outlet pressure from the pump P is applied to control chamber 55 of the exhalation valve 50, thereby causing diaphragm 54 of that valve to be in its closed position against valve seat 54a, as illustrated in FIG. 3. Accordingly, the flow of air at the outlet of pump P passes from the pump and the air delivery tube 48 via the inlet port 51 and the outlet port 52 of the exhalation valve 50 to the patient.

Figure 5A:
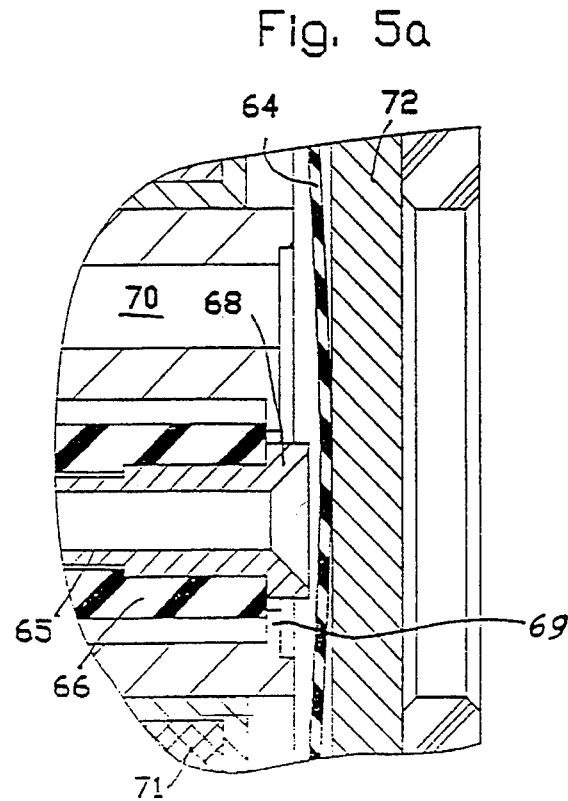

Now, if the current through the solenoid coil 71 is reduced to zero, diaphragm 64 of control valve 60 will assume the position illustrated in FIGS. 5 and 5a. In this position, the pre-stressed condition of the elastomeric tube 66 moves the hollow stem 65 rightwardly until the edge of the elastomeric tube engages flange 69, thereby closing the passageway between the inlet port 61 and the control port 62. The tip 68 of the hollow stem 65, however, is still in contact with the diaphragm 64, so that the passageway between the tip and the diaphragm is also closed. Accordingly, the pressure existing within control chamber 55 is trapped within that control chamber. However, since the armature 72 is in its rightmost position, very little force is applied by diaphragm 64 against the outer tip 68 of the hollow stem 65. Therefore a small additional pressure applied to the diaphragm from the control port 62 will displace the diaphragm (rightwardly, FIGS. 5 and 5a), to open a passageway between the diaphragm and the outer tip 68 of the hollow stem, thereby venting to the atmosphere the pressure within control chamber 55 via the atmospheric vent 63. Thus, when the patient exhales via the exhalation port 53, diaphragm 54 of the exhalation valve unseats from seat 54a to thereby connect the outlet port 52 to the exhalation port 53, permitting the patient to exhale to the atmosphere.

It will thus be seen that the larger the magnitude of current passed through coil 71 during exhalation, the greater will be the force applied by the armature 72 of the solenoid against diaphragm 64 resisting the opening of the passageway between the diaphragm and the tip 68 of the hollow stem 65 leading to the atmospheric vent 63, and therefore the greater will be the fixed pressure applied by control chamber 55 during inspiration and exhalation. Accordingly, the exhalation pressure may be preset according to the particular case by control knob 75.

While the invention has been described with respect to two preferred embodiments, it will be appreciated that these are set forth merely for purposes of example, and that many other variations, modifications and applications of the invention may be made.

I claim:

1. A reciprocating pump particularly useful in ventilator apparatus, comprising:

a pump housing having an inlet at one end, an outlet at another end, and a cylinder between said inlet and outlet;

a piston reciprocatable axially within said cylinder and dividing its interior into an inlet chamber communicating with said inlet, and an outlet chamber communicating with said outlet;

a fixed wall within said inlet chamber and having a passageway therethrough communicating with said inlet;

a drive housing fixed to said wall and including a motor having a rotor rotatable by the energization of said motor;

a nut rotatable within said drive housing and fixed to said rotor to rotate therewith;

and a screw threadedly coupled at one end to said nut and fixed at its opposite end to said piston;

said piston being supported by a single rotatable bearing between said nut and the drive housing and a seal between said piston and the cylinder.

2. The pump according to claim 1, wherein said piston is substantially unrestrained for axial and rotary movement such that forward and reverse rotation of the nut by the motor reciprocates said screw and the piston fixed thereto axially of the cylinder, and also permits the screw and the piston fixed thereto to rotate with respect to the cylinder to thereby even out wear said seal between the piston and cylinder.

3. The pump according to claim 1, further including a noise isolator interposed between said rotatable nut and said drive housing.

4. The pump according to claim 1, wherein said pump housing further includes:

an inlet conduit connecting said pump housing inlet to both said chambers and having one-way valves which permit fluid flow only in the direction from said pump housing inlet into the respective chamber;

and an outlet conduit connecting said pump housing outlet to both said chambers and having one-way valves which permit fluid flow only in the direction from the respective chamber to said pump housing outlet.

5. Respirator apparatus including a pump according to claim 1, and an exhalation valve coupled to the pump housing outlet via a coupling fitting, said coupling fitting including a one-way valve which is normally closed, but which is automatically opened by a negative pressure within said coupling fitting to connect the interior of said coupling fitting to the atmosphere.

6. The pump according to claim 1, further including a tubular sleeve fixed to said drive housing in alignment with said screw for receiving and enclosing one end of said screw opposite to that fixed to said piston.

7. The pump according to claim 6, wherein said tubular sleeve includes a lubricating wick for lubricating the screw when received therein.

8. The pump according to claim 1, further including a bellows enclosing said screw and having one end fixed to said wall and the opposite end engaging said piston.

9. The pump according to claim 8, wherein said outlet includes a one-way valve permitting fluid flow only in the direction from the outlet chamber outwardly of the pump housing.

10. The pump according to claim 9, wherein said piston includes a one-way valve permitting fluid flow only in the direction from the inlet chamber to the outlet chamber.

* * * * *